United States Patent [19]

Brownlee et al.

[11] 4,340,977
[45] Jul. 27, 1982

[54] CATENARY MITRAL VALVE REPLACEMENT

[76] Inventors: Richard T. Brownlee, #101, 1780 Fort St., Victoria, British Columbia, Canada, V8R 1J5; Lawrence N. Scotten, 814-Langham Ct., Victoria, British Columbia, Canada, V8V 4J2; David K. Walker, 1576 Cedarglen Rd., Victoria, British Columbia, Canada, V8N 2B2

[21] Appl. No.: 188,817
[22] Filed: Sep. 19, 1980
[51] Int. Cl.$^3$ .................................................. A61F 1/22
[52] U.S. Cl. .......................................... 3/1.5; 137/846
[58] Field of Search ............................... 3/1.5; 137/846

[56] References Cited

U.S. PATENT DOCUMENTS

| 3,608,097 | 9/1971 | Bellhouse et al. | 3/1.5 |
| 3,655,306 | 4/1972 | Ross et al. | 3/1.5 X |
| 3,710,744 | 1/1973 | Goodenough et al. | 3/1.5 X |
| 3,714,671 | 2/1973 | Edwards et al. | 3/1.5 |
| 3,739,402 | 6/1973 | Cooley et al. | 3/1.5 |
| 3,755,823 | 9/1973 | Hancock | 3/1.5 |
| 4,172,295 | 10/1979 | Batten | 3/1.5 |
| 4,222,126 | 9/1980 | Boretos et al. | 3/1.5 |

FOREIGN PATENT DOCUMENTS 1264471 2/1972 United Kingdom ................ 3/1.5

OTHER PUBLICATIONS

"Heart Valve Replacement With Autologous Fascia Lata", by M. I. Ionescu et al., The Journal of Thoracic & Cardiovascular Surgery, vol. 60, No. 3, Sep. 1970, pp. 331-354.

"Frame-Mounted Tissue Heart Valves: Technique of Construction", by I. T. Bartek, Thorax (1974), 29, pp. 51-55.

Primary Examiner—Ronald L. Frinks

[57] ABSTRACT

Mitral heart valve comprising a stent including a circular base and a pair of upstanding diametrically opposed struts, separating a pair of diametrically opposed arcuately shapes depressed reliefs, each such relief being bounded by a smooth curve interconnecting the struts to the circular base. A flexible, durable, biocompatible covering is secured to the stent and provides two equal opposed preset flappably movable valve cusps secured along the smooth curve defining the perimeter of the reliefs. The valve cusps each are preformed and preset so that the perimeter of the biocompatible covering along the free edge of each of the cusps between the tips of each associated strut is so related to the circumference of the circular base that, when the valve is in its forced open position, the cross-sectional area of the exit is substantially equal to the cross-sectional area of the inside of the circular base. When the valve is in its relaxed and natural position, the shape of the cusps is such that the free edges of the cusps sealingly meet in substantially wrinkle-free form at a line of apposition in the plane defined by the tips of the struts and the axis of the valve and follow the approximate shape of a catenary curve.

10 Claims, 3 Drawing Figures

CATENARY MITRAL VALVE REPLACEMENT

BACKGROUND OF THE INVENTION

1. Field of the Invention

This invention relates to fluid valves, and more particularly, to such fluid valves which permit fluid flow in one direction and prevent fluid flow in the opposite direction. Such a valve may be used as a replacement valve in a human heart or in artificial heart pumps.

2. Description of the Prior Art

Heart valve disease in advanced forms causes severe disability and ultimately death. The quality and length of life for patients suffering from valve disease can be remarkably improved by surgical treatment, which usually involves the total replacement of the diseased valve with a prosthetic valve.

In the two decades since the first successful implantation in a human, nearly 50 different valve types have been introduced and many have been discarded; of those remaining, two basic types are in use—those constructed of human or animal tissues (tissue valves) and those constructed of cloth, metals, carbon, and plastic components (nontissue or mechanical valves).

These devices have come in various forms of flexible unicusp, bicuspid, and tricuspid valves, ball valves and "butterfly" or flapper valves.

Significant late complications following implantation of these valves can occur and are related to valve design and materials. Present valve replacements do not permit restoration of normal pressure-flow dynamics at all levels of cardiac function. Thus, there is still no clearcut choice for the surgeon and the search for the ideal replacement heart valve is continuing.

In addition artificial heart pumps are now known which have been developed to simulate the action of the human heart. Critical components in the artificial heart pump include the fluid control valves and they must operate faultlessly for an indefinite period of time with a mechanical action that does not produce excessive blood damage (haemolysis).

Stented tissue valves, that is, supported valvular grafts which may be either xenografts (heterografts) or allografts (homografts), have been used as replacement heart valves. (See, for example, Carpentier et al., J. Thorac. Cardiovasc. Surg. 68:771 (1974); Zuhdi et al., Ann. Thorac. Surg. 17:479 (1974); Horowitz et al., J. Thorac. Cardiovasc. Surg. 767:884 (1974)). In general, such grafts have been mounted on supporting frames (stents) which provide rigid orifice rings (See Weldon et al., J. Surg. Research 6:548 (1966)). Some stents have included struts capable of flexing inwardly to a limited extent, thereby reducing stresses imposed on the grafts and decreasing possible erosion of surrounding tissues of the patient (See Sugie et at., J. Thorac. Cardiovasc. Surg. 57:455 (1969); and Hardy, Human Organ Support and Replacement, 338 et. seq.). Despite the encouraging results with prosthetic tissue heart valves and in contrast to non-tissue prosthetic valves, there is a continuing need for improvement, particularly with regard to the hydrodynamic performance and long-range durability of the tissue valves.

The art is still faced with the desirability of providing an improved stent for a tissue (xenograft or allograft) heart valve which is capable of yielding to a limited extent in response to forces which tend to alter the configuration and circumference of the orifice ring, thereby improving the long-range reliability of the valves. Accordingly, continued efforts are being made to develop more efficient, reliable and biocompatible prostheses.

The results of such continued efforts are evidenced in heart valves which are disclosed in issued U.S. patents.

U.S. Pat. No. 2,832,078 issued Apr. 29, 1958 to D. T. Williams discloses an aortic heart valve including a slotted cylindrical shell with an internal three-sac membrane to provide opening and closing ports, which seal at the centre of the cylindrical shell.

U.S. Pat. No. 3,197,788 issued Aug. 3, 1965 to F-J Segger, provides an aortic heart valve including a deformable cone-shaped cusp-supporting ring, with the cusps having smooth curved surfaces.

U.S. Pat. No. 3,548,418 issued Dec. 22, 1970 to W. W. Angell et al., provides a graft-supporting ring for grafting porcine aortic valves in which the ring is generally in the form of the residual portion of a conical shell, having three struts, the ring being completely covered and having three internal depressed valve cusps.

U.S. Pat. No. 3,570,014 issued Mar. 16, 1971 to W. D. Hancock provides a stent for aortic and mitral heart valves in which the stent includes a ring and three support arms rising therefrom, to which commissures and cusps of a heart valve are attached.

U.S. Pat. No. 3,714,671 issued Feb. 6, 1973 to W. S. Edwards et al. provides a stent for supporting a tricuspid heart valve, in which the ring comprises portions of ellipses, in which the upstanding portions are covered with fabric and which terminate in radial wings, and to which three valve cusps are sutured, the valve cusps having straight trimmed edges, and being supported without tension.

U.S. Pat. No. 3,736,598 issued June 5, 1973 to B. J. Bellhouse et al. provides and aortic valve including a ring having three legs folded to U-shaped sections to which are attached three valve cusps whose free edges meet in radial planes of abutment.

U.S. Pat. No. 3,739,402 issued June 19, 1973 to D. A. Cooley et al., provides a graft support for a bicusp valve which includes a frusto-conical ring and a pair of inverted frusto-conical segments defining struts, all provided with a fabric cover, to which are secured a pair of cusps whose upper edges lie adjacent to each other to form the valve opening.

U.S. Pat. No. 3,744,062 issued July 10, 1973 to V. Parsonnet provides a heart valve construction including a stent having three lower arcuate portions and three upstanding posts, to which a fabric sheath is secured, and from which three valve leaflets, each having an arcuate edge and a straight edge are secured, so that the straight edges provide an upper meeting closure.

U.S. Pat. No. 3,755,823 issued Sept. 4, 1973 to W. D. Hancock provides a stent for heart valves in the form of a flexible stent including a ring having three spaced-apart apexes to which a cloth sleeve is attached and to which three valve cusps are attached, so that the free edges sag towards the centre, at which point they meet at a central, slightly raised point. This valve utilizes a whole porcine aortic valve which is pretreated before mounting on the stent.

U.S. Pat. No. 3,938,197 issued Feb. 17, 1976 to S. Milo provides a heart valve including a ring to which are attached a plurality of flat valve flaps whose free edges all meet in abutting relation.

U.S. Pat. No. 3,983,581 issued Oct. 5, 1976 to W. W. Angell et al. provides a heart valve stent of a particular shape, to which a covering is attached, and from which three valve cusps are attached so that their free edges meet at three commissures, and so that their common points meet at a central depression. A whole porcine xenograft is mounted to the stent.

U.S. Pat. No. 4,035,849 issued July 19, 1977 to W. W. Angell et al. provides a heart valve stent of a particular shape, to which a covering having a bead along its perimeter is attached and from which three valve cusps are attached, so that their free edges meet at three commissures and so that their common points meet at a central depression. A whole porcine xenograft is mounted to the stent.

U.S. Pat. No. 4,084,268 issued Apr. 18, 1978 to M. I. Ionescu et al. provides a heart valve including a dish-shaped cloth-covered stent having three upright posts, to which three cusps are attached, the cusps meeting at their upper edges at a flat closed portion, and in which the knots of the stitches are covered by a pledget and cover. This valve uses pretreated bovine pericardium for its three leaflets.

U.S. Pat. No. 4,106,129 issued Aug. 15, 1978 to A. F. Carpentier et al. provides a heart valve including a deformable wire-frame stent having three inverted U-shaped commissure supports, to which are secured a cover, and from which are suspended three valve leaflets meeting along the commissures. A whole porcine xenograft is mounted to the stent.

U.S. Pat. No. 4,164,046 issued Aug. 14, 1979 to D. A. Cooley provides a mitral or tricuspid valve replacement which is based on an open ring stent.

U.S. Pat. No. 4,172,295 issued Oct. 30, 1979 to R. J. Batten provides a tricuspid heart valve dish-shaped cloth-covered stent having three upright ports to which are attached three cusps meeting at their upper edges at a flat closed portion, in which the knots of the stitches are covered by a pledget and cover, and in which securing holes are provided between the cusps.

U.S. Pat. No. 4,178,639 issued Dec. 18, 1979 to J. C. Bokros provides a heart valve having an annular valve body and a pair of pivotally secured valve leaflets.

In spite of all these prior patents, improvements are still required to provide improved valves which: provide minimal obstruction to the flow of blood; have smooth surfaces to minimize haemolysis; must not be too slow in closing, thereby permitting a substantial and undesirable reflux caused by the relatively high head pressure of the pump system; in opening and closing, there should be a minimum amount of mechanical stress and strain to the valve which would materially contribute to shortening the life of the valve; provide adequate support for attachment within the heart; minimize adverse clotting effects; should not create significant turbulence in the blood stream in both systole and diastole, which can damage blood elements; provide accuracy in the size and shape of the cusps; provide accuracy in the shape and size of the stent ring; have improved reliability by minimizing stresses in the flexing cusps tissue; incorporate flexibility and deformability in their functional operation; and improve the structural alignment of the tissue relative to the stent.

SUMMARY OF THE INVENTION

Aims of the Invention

Accordingly, an object of this invention is to provide an improved one-way valve.

Another object of this invention is to provide an improved one-way valve which may be used in artificial heart pumps as well as for heart valve replacements. Further objectives of this invention are to provide heart valves having the following characteristics:

1. free flow central orifice configuration;
2. rapid opening and closing;
3. potential minimal compressive and tensile stress distribution on flexing leaflets and hence improved valve reliability;
4. high ratio of available valve flow area to implant site area;
5. relative ease of fabrication of all sizes compared to other tissue type valves;
6. minimal obstruction to the left ventricular outflow tract;
7. negligible retrograde flow;
8. maximal conformity to the natural anatomic valve configuration;
9. minimal thromboembolic potential;
10. ease of handling and insertion; and
11. silent operation.

Statements of Invention

By one embodiment of this invention, a mitral heart valve is provided comprising a stent including a circular base and a pair of upstanding diametrically opposed struts, separating a pair of diametrically opposed arcuately shaped depressed reliefs, each such relief being bounded by a smooth curve interconnecting the struts to the circular base; a flexible, durable, biocompatible covering secured to the stent and providing two equal opposed preset flappably movable valve cusps secured along the smooth curve defining the perimeter of the reliefs; the valve cusps each being performed and preset so that the perimeter of the biocompatible covering along the free edge of each of the cusps between the tips of each associated strut being so related to the circumference of the circular base that, when the valve is in its forced open position, the cross-sectional area of the exit is substantially equal to the cross-sectional area of the inside of the circular base, and, when the valve is in its relaxed and natural closed position, the shape of the cusps is such that the free edges of the cusps sealingly meet in substantially wrinkle-free form at a line of apposition in the plane defined by the tips of the struts and the axis of the valve and follow the approximate shape of a catenary curve.

By another embodiment of this invention, a method is provided for making a mitral heart valve comprising the steps of: (a) providing a stent including a circular base and a pair of diametrically opposed reliefs, the height of the struts being a selected value derived from the outside circumference of the circular base; (b) providing a shape for the cusps in their closed position by requiring that the length of cusp tissue from the strut to the free edge provides a catenary or other curve of equal length.

Other Features of this Invention

By a feature of the embodiments of this invention, the struts are made to be flexibly elastically deformable to minimize stresses on the valve cusps when the valve closes.

By another feature thereof, the struts are substantially identical.

By a further feature thereof, the free edges of the cusps follow a precise catenary curve in the closed position.

By a further feature thereof, the reliefs are symmetrically disposed equidistant from the struts.

By a feature of the embodiments of this invention, the valve cusps are formed preferably of pericardium treated with glutaraldehyde.

By a further feature, the valve cusps are formed of other flexible materials e.g., polyurethane-type compounds.

By another feature of this invention, the height of the struts is one-quarter of the outside circumference of the circular base.

By yet another feature thereof, the cusps are secured to each other and to the struts by sutures.

By a further feature of this invention, the smooth curve interconnecting the struts is a parabola.

By yet another feature of this invention, the stent is formed of a flexible, elastically deformable material, so that the struts may flex slightly.

By still another feature, the material is polypropylene or is an acetal copolymer.

By a still further feature, the valve cusps are formed of bovine, porcine or human fascia lata or dura mater, or of polyurethane.

The heart valve provided herein in one preferred embodiment is designed specifically for the mitral position which has the bicuspid character of the natural mitral valve. Such a design more likely takes advantage of the anatomic configuration and flow patterns of the natural left ventricle than, for example, a tricuspid tissue valve or a non-tissue valve in the mitral position. When closed, a bicuspid valve has the advantage of presenting minimal obstruction of the ventricular outflow tract.

BRIEF DESCRIPTION OF THE DRAWINGS

In the accompanying drawings.

DESCRIPTION OF PREFERRED EMBODIMENT

Figure 1:
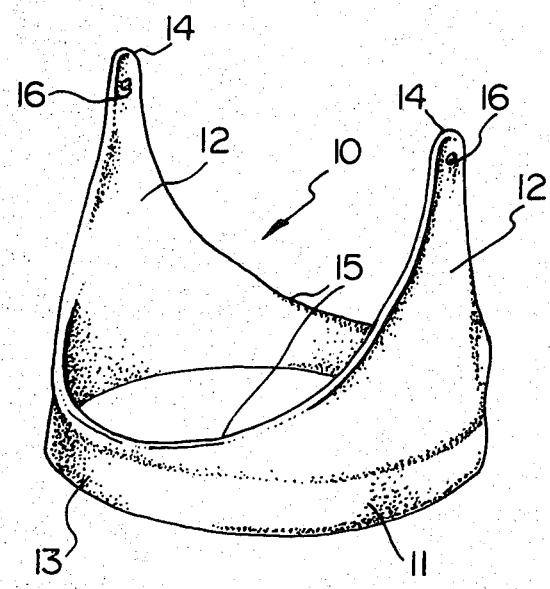
FIG. 1 is a perspective view of the stent forming part of the mitral valve replacement of an embodiment of this invention.

Description of FIG. 1

As seen in FIG. 1, the stent includes diametrically opposed reliefs which are slightly splayed from the vertical axis of the valve to allow for tissue anchoring at the valve outlet without causing obstruction to flow with the valve fully open. The stent also includes a low cylindrical base member or ring 11. Disposed about the cylindrical base member or ring 11 are a pair of identical, diametrically opposed struts 12 between which are a pair of identical, diametrically opposed reliefs 13. The struts can, of course, be less than true conical segments and still provide a stent 10 which can be used in providing the mitral valve replacement of an embodiment of this invention.

The stent 10 is made as light and unbulky as is compatible with the needed strength and with avoidance of sharp edges. Preferably it is made of a flexible elastically deformable material, i.e., synthetic plastic materials, e.g. polypropylene or acetal copolymer, so that the struts 12 may flex slightly. The struts 12 have rounded extremities 14 and are connected to the cylindrical base member or ring 11 by smooth curves 15 to give the reliefs 13 an arcuate shape. Each strut 12 has anchor openings 16.

Figure 2:
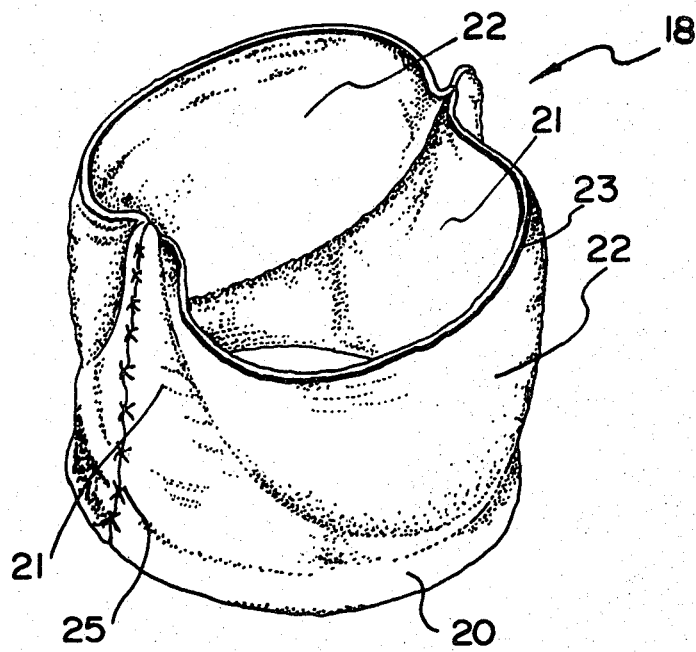
FIG. 2 is a perspective view of the mitral valve of an embodiment of this invention, in the open position.
Figure 3:
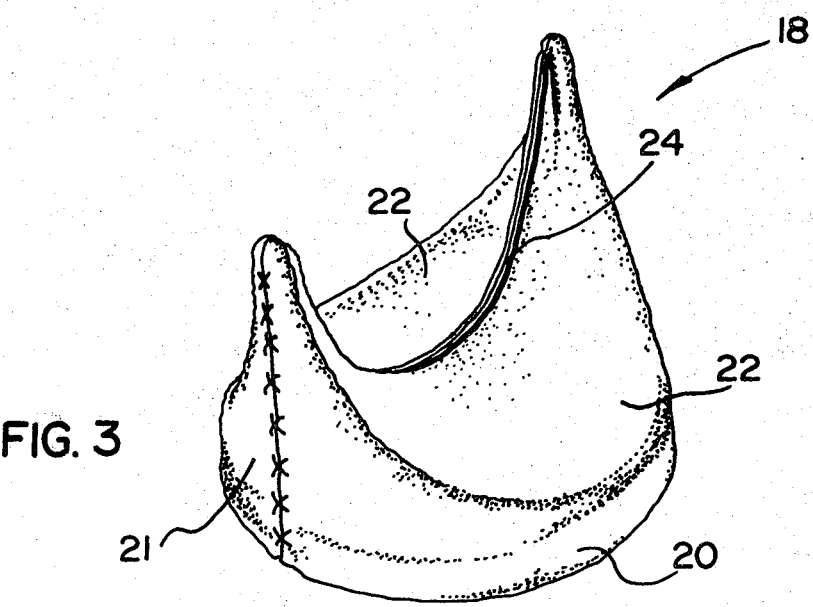
FIG. 3 is a perspective view of the mitral valve of an embodiment of this invention in the closed position.

Description of FIGS. 2 and 3

The mitral valve 18 is formed on the stent 10 by a suitable covering material so secured to the cylindrical base member or circle 11 to provide a pair of opposed surfaces 21 secured to the struts 12 of the stent 10 and a pair of opposed cusps 22 which are flappably movable. The perimeter 23 at the free edges of the cusps 22 is preferably of such length that when the free edges meet the valve is closed to form a catenary or other curve 24 of length equal to the perimeter 23.

In the embodiment of this invention as shown in FIGS. 2 and 3, the mitral valve 18 in its closed position has two equal cusps 22 which form a line of apposition in the plane defined by the tip of each stent strut 12 and the axis of symmetry of the valve 18. In the open position, the valve 18 provides an approximately cylindrical shape of tissue with an exit area equal to the inside area of the cylindrical member or circular base 11 of the stent 10.

In this embodiment, the length 23 of tissue between the tips of each stent strut 12 in the closed position equals half the circumference of the exit aperture of the valve 18. This is achieved by having a curved closure line which appears to be like a line dropping from the stent strut tips 14 towards the cylindrical base member or ring 11. The curve is preferably a catenary, i.e., the curve formed by a uniform chain hanging freely between two points but may assume other curved configurations provided the specified tissue length is adhered to.

Description of Other Embodiments of the Invention

Calf pericardium was selected as the material for construction of the valve cusps since, when treated with glutaraldehyde, it has acceptable durability and biocompatibility. Other naturally-occurring materials, e.g., bovine, porcine, human (pericardium, fascia lata, dura mater) or synthetic materials, e.g. polyurethanes e.g. that known by the Trade Mark of AVCOTHANE of acceptable durability and biocompatibility may also be used. A flexible stent made of acetal copolymer, is preferably used since it allows flexibility and thereby provides greater valve durability.

Description of Preparation of Embodiment of the Invention

In the preparation of one variant embodiment of this invention, a prototype stent 10 was machined from an acetal copolymer rod. The height of the strut 12 above the cylindrical base member or ring 11 was equal to one-quarter of its outside curcumference. The shape of the cusps 22 in the closed position was determined by requiring that the lengths of tissue shown for the open valve 18 from the tip 14 of the strut 12 to the free edge of the cusps 22 should form catenaries or other suitable curves in the closed position. The sectional contours of the cusps 22 in the closed position were then generated. A mold was then made around which each cusp 22 could be formed. The moist tissue for the cusps 22 was attached to the stent 10, then sutures 25 were used to secure the cusps to each other and to the tips 14 of the stent struts 12. The valve 18 was fixed in the closed position using 0.625% glutaraldehyde solution while the shape of the cusps 22 was maintained by cotton batting and by a negative mandrel shape. The shape was further maintained after initial fixation by cotton batting once the negative mandrel molding was removed.

Description of Comparison of Operation of an Embodiment of this Invention

The mitral replacement valve 18 of an embodiment of this invention was compared against different conventional types of prostheses using a hydromechanical apparatus which provided a realistic simulation of heart geometries, pressures, and flows. The hydrodynamic performance of each of the valves tested was compared at three different pulse rates (60, 80, and 120 beats per minute). The three measures used to characterize valvular performance were:

Table I, mean and maximum transmitral pressure difference
Table II, observed and calculated open valve area
Table III, total transmitral energy loss per cycle

TABLE I

| | Transmitral pressure difference; mean, maximum (mmHg) at | | |
|---|---|---|---|
| Valves | 60 beats/min | 80 beats/min | 120 beats/min |
| (1) Bicusp | 1.3, 11.5 | 1.8, 12.0 | 2.9, 11.0 |
| (2) Bjork-Shiley, c.c. | 1.2, 14.2 | 2.1, 13.3 | 4.8, 13.0 |
| (3) St. Jude Medical | 1.3, 13.6 | 2.9, 15.0 | 5.0, 13.4 |
| (4) Hall-Kaster | 1.4, 16.0 | 1.9, 14.4 | 5.5, 15.8 |
| (5) Ionescu-Shiley | 1.6, 7.8 | 3.0, 11.0 | 5.9, 13.4 |
| (6) Omniscience | 1.8, 15.6 | 2.5, 14.7 | 6.2, 16.8 |
| (7) Bjork-Shiley | 1.6, 14.2 | 2.9, 14.4 | 6.9, 13.9 |
| (8) Lillehei-Kaster | 3.9, 18.2 | 3.5, 14.1 | 8.4, 17.0 |
| (9) Carpentier-Edwards | 2.9, 15.5 | 4.6, 17.5 | 8.7, 18.7 |
| (10) Starr-Edwards | 4.1, 14.1 | 6.2, 18.1 | 11.4, 22.1 |
| (11) Hancock | 4.4, 16.9 | 6.7, 20.4 | 13.4, 25.4 |

Note:
Bracketed numbers indicate order of merit with (1) being the best valve and (11) the worst.

TABLE II

| | Open valve area; calculated, observed (cm$^2$) at | | |
|---|---|---|---|
| Valves | 60 beats/min | 80 beats/min | 120 beats/min |
| (1) Bicusp | 3.0, 3.9 | 3.6, 4.1 | 5.3, 4.7 |
| (2) Bjork-Shiley, c.c. | 3.6, | 4.2, | 4.2, |
| (3) St. Jude Medical | 2.8, | 3.5, | 3.8, |
| (4) Hall-Kaster | 2.9, | 3.7, | 3.3, |
| (5) Omniscience | 2.7, | 3.2, | 3.0, |
| (6) Ionescu-Shiley | 2.7, 2.9 | 2.4, 3.2 | 2.9, 3.2 |
| (7) Bjork-Shiley | 2.8, | 3.5, | 2.8, |
| (8) Lillehei-Kaster | 2.0, | 2.7, | 2.3, |
| (9) Carpentier-Edwards | 2.1, 2.0 | 2.1, 2.0 | 2.2, 2.1 |
| (10) Hancock | 1.9, 1.5 | 1.5, 1.6 | 1.9, 1.7 |
| (11) Starr-Edwards | 1.7, | 1.7, | 1.7, |

Note:
Bracketed numbers indicate order of merit with (1) being the best valve and (11) the worst.
Non tissue type valves do not have an observed area.

TABLE III

| | Total transmitral energy loss (%) at | | |
|---|---|---|---|
| Valves | 60 beats/min | 80 beats/min | 120 beats/min |
| (1) Bicusp | 7 | 8 | 7 |
| (2) Ionescu-Shiley | 7 | 9 | 11 |
| (3) Carpentier-Edwards | 9 | 9 | 11 |
| (4) Omniscience | 9 | 10 | 12 |
| (5) Hall-Kaster | 10 | 11 | 12 |
| (6) St. Jude Medical | 10 | 12 | 13 |
| (7) Bjork-Shiley, c.c. | 12 | 12 | 13 |
| (8) Starr-Edwards | 7 | 8 | 14 |
| (9) Bjork-Shiley | 15 | 16 | 18 |
| (10) Lillehei-Kaster | 15 | 17 | 18 |
| (11) Hancock | 12 | 13 | 19 |

TABLE III-continued

| | Total transmitral energy loss (%) at | | |
|---|---|---|---|
| Valves | 60 beats/min | 80 beats/min | 120 beats/min |
| Total model ventricular energy (Joules) | 0.935 | 1.066 | 1.105 |

Note:
Bracketed numbers indicate order of merit with (1) being the best valve and (11) the worst.

The Bjork-Shiley may be described as a valve which utilizes a single spherical tilting disc occluder. The disc is made from pyrolytic carbon and the metal housing is made of a metal known by the Trade Mark STELLITE. Cloth of a polytetrafluoroethylene known by the Trade Mark TEFLON is used for the suturing ring.

The Omniscience may be described as a valve which utilizes a single pivoting curvilinear - shell occluder. The disc is made from pyrolytic carbon and the metal housing is made of titanium. The suturing ring is made of knitted polyester.

The Bjork-Shiley (cc) may be described as a valve which utilizes a single convexo-concave tilting disc occluder. The disc is made of pyrolytic carbon and the metal housing is made of STELLITE. The suturing ring is made of knitted TEFLON. (See Canadian Patent 1,066,853)

The Hall-Kaster may be described as a valve which utilizes a single spherical pivoting disc occluder. The disc is made from pyrolytic carbon and the metal housing is made of titanium. The suturing ring is made of knitted TEFLON.

The Starr-Edwards may be described as a valve which utilizes a silicone rubber ball occluder. The metal housing is made of STELLITE. The suturing ring is made of knitted TEFLON and polypropylene.

The Carpentier-Edwards may be described as a valve which utilizes a glutaraldehyde preserved flexible support mounted porcine xenograft. The flexible support is comprised of wire frame formed of a wire known by the Trade Mark ELGILOY, having an insert of a material known by the Trade Mark REEMAY, with a support of a synthetic plastic known by the Trade Mark MYLAR and a TEFLON cloth. (See Canadian Patent 1,069,652 and U.S. Pat. No. 4,106,129).

The Hancock may be described as a valve which utilizes a glutaraldehyde preserved flexible support mounted porcine xenograft. The flexible support is comprised of polypropylene, STELLITE, silicone foam, and knitted synthetic fabric known by the Trade Mark DACRON. (See U.S. Pat. No. 3,755,823).

The St. Jude Medical may be described as a valve which utilizes two center opening tilting disc occluders. The discs and housing are made from pyrolytic carbon. The suturing ring is made of a DACRON velour. (See U.S. Pat. No. 4,178,639)

The Ionescu-Shiley may be described as a valve which utilizes bovine pericardial xenograft material for construction of three equal cusps mounted on a symmetrical titanium frame covered with DACRON cloth. The suturing ring is also made of DACRON cloth. (See U.S. Pat. No. 4,084,268)

The Lillehei-Kaster may be described as a valve which utilizes a free - floating pyrolytic carbon disc for an occluder. The housing is made from titanium and the suturing ring is made from DACRON cloth.

The Bicusp Mitral Valve is the valve of an embodiment of the present invention as described in FIGS. 1–3.

From the results shown in the Tables, the bicusp mitral valve of an embodiment of this invention, tested under simulated conditions in a model left heart as described have shown significantly reduced obstruction of flow through the valve demonstrated by showing the smallest transmitral pressure, largest open area, and least transvalvular energy loss as compared to existing devices.

As noted above, the hydrodynamic performance of the bicusp valve has been assessed by comparison with existing prostheses, namely, with seven non-tissue valves and three tissue valves. The parameters measured were: mean and maximum transvalvular pressure difference; maximum observed or calculated open area; and total transmitral energy loss. The bicusp mitral valve of an embodiment of this invention demonstrates performance superior to all tested prostheses as assessed by these parameters.

Summary

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

We claim:

1. A mitral heart valve comprising: a stent including a circular base and a pair of upstanding diametrically opposed struts, separating a pair of diametrically opposed arcuately shaped depressed reliefs, each said said relief being bounded by a smooth curve interconnecting the struts to the circular base; a flexible, durable, biocompatible covering secured to said stent and providing two equal opposed preset flappably movable valve cusps secured along said smooth curve defining the perimeter of said reliefs; said valve cusps each being preformed and preset so that the perimeter of said biocompatible covering along the free edge of each of said cusps between the tips of each associated strut being so related to the circumference of the circular base that, when the valve is in its forced open position, the cross-sectional area of the exit is substantially equal to the cross-sectional area of the inside of said circular base, and, when said valve is in its relaxed and natural closed position, the shape of said cusps is such that the free edges of the cusps sealingly meet in substantially wrinkle-free form at a line of apposition in the plane defined by the tips of said struts and the axis of the valve and follow the approximate shape of a catenary curve.

2. The valve of claim 1 wherein said struts are substantially identical.

3. The valve of claim 2 wherein said reliefs are symetrically disposed equidistant from said struts.

4. The valve of claim 2 wherein the free edges of said cusps follow a precise catenary curve.

5. The valve of claim 4 wherein the valve cusps are formed of pericardium treated with glutaraldehyde.

6. The valve of claim 5 wherein said cusps of pericardium are secured to each other and to said struts by sutures.

7. The mitral heart valve of claim 5 wherein said smooth curve interconnecting said struts is a parabola.

8. The mitral heart valve of claim 1 wherein said stent is formed of a flexible, elastically deformable material, so that said struts may flex slightly.

9. The mitral heart valve of claim 8 wherein said material is selected from the group consisting of polypropylene or an acetal copolymer.

10. The mitral heart valve of claim 1 wherein the valve cusps are formed from material selected from the group consisting of bovine, porcine or human fascia lata or dura mater, or of polyurethane.

* * * * *